(12) United States Patent
Slack

(10) Patent No.: US 6,487,432 B2
(45) Date of Patent: Nov. 26, 2002

(54) METHOD AND SYSTEM FOR SELECTING AND DISPLAYING MEDICAL IMAGE DATA

(75) Inventor: Christopher C. Slack, New Berlin, WI (US)

(73) Assignee: GE Medical Systems Global Technologies Company LLC, Waukesha, WI (US)

( * ) Notice: Subject to any disclaimer, the term of this patent is extended or adjusted under 35 U.S.C. 154(b) by 220 days.

(21) Appl. No.: 09/729,602

(22) Filed: Dec. 4, 2000

(65) Prior Publication Data

US 2002/0068863 A1 Jun. 6, 2002

(51) Int. Cl.$^7$ .............................. A61B 5/055; A61B 6/02
(52) U.S. Cl. ........................... 600/407; 378/4; 378/901; 382/131
(58) Field of Search ............................ 600/407, 410, 600/425, 436, 437; 378/4, 901; 703/11; 382/128, 131, 154, 302

(56) References Cited

U.S. PATENT DOCUMENTS 5,722,408 A * 3/1998 Dehner et al. .............. 600/407
6,112,109 A * 8/2000 D'Urso ....................... 600/407

* cited by examiner

Primary Examiner—Peter Nerbun
(74) Attorney, Agent, or Firm—Quarles & Brady, LLP; Carl Horton

(57) ABSTRACT

A CT system acquires a succession of 2D slice images which are combined to produce a 3D image data set. A projection image is produced from the 3D image data set and serves as an index which enables the operator to select a particular region of interest in the acquired 3D image data set. A specified number and orientation of slice images are then produced through the region of interest.

16 Claims, 3 Drawing Sheets

METHOD AND SYSTEM FOR SELECTING AND DISPLAYING MEDICAL IMAGE DATA

BACKGROUND OF THE INVENTION

The field of the invention is medical imaging and particularly, methods for enabling physicians to select and display diagnostic images from image data acquired with medical imaging systems.

There are many imaging modalities used to acquire medical images suitable for diagnosing disease or injury. These include x-ray, CT, magnetic resonance imaging (MRI), ultrasound and nuclear medicine systems. These medical imaging systems are characterized by their ability to acquire large amounts of image data during a patient scan. The image data may be acquired directly as a three-dimensional ("3D") image, but in most cases the image data is acquired as a series of contiguous two-dimensional ("2D") slice images that may or may not be combined to form a 3D image.

In many cases the location of the disease or injury is well defined and the physician can prescribe a scan which acquires an appropriate amount of image data at and around the known location. For example, the region of interest in a scan of a knee, shoulder or elbow to diagnose a joint injury can be precisely defined. The acquired image data in such cases is relatively limited in scope and its display relatively straight forward. For example, 10 to 1000 2D slices may be acquired and viewed one at a time by the physician to diagnose the injury.

As imaging systems have improved in speed and image quality, their medical applications have expanded. One such application is the use of an x-ray CT system in a trauma center to help find and diagnose injuries. In such applications huge amounts of image data may be acquired (e.g. 300 to 1000 2D slices) over a large region of the patient (e.g. chest/abdomen/pelvis). As a result, the physician is faced with the formidable task of viewing all the acquired 2D slice image data to locate the region of interest where the injury has occurred and then to select the diagnostically most useful images. This procedure is time consuming and monotonous.

SUMMARY OF THE INVENTION

The present invention is a method and system for enabling large amounts of image data to be displayed such that the diagnostician can easily locate a region of interest in the field of view of the acquired image data and precisely specify a set of 2D diagnostic images that encompass the region of interest. More particularly, the acquired image data is processed to produce a 3D image data set; the 3D image data set is used to produce an index image on a display which depicts the subject of the scan in 3D throughout the field of view of the acquired image data; a pointing tool is provided to enable the diagnostician to select a region of interest in the index image; and a prescription tool is provided to enable the diagnostician to specify a set of 2D diagnostic images which depict the subject of the scan as a corresponding set of 2D slices through the region of interest. The prescription tool enables the number, size and orientation of the 2D slices to be specified by the diagnostician such that the number of diagnostic images may be limited to a reasonable number while providing maximum diagnostic information.

DESCRIPTION OF THE PREFERRED EMBODIMENT

The present invention can be practiced in many different medical imaging modalities including computed tomography (CT), magnetic resonance (MR), and ultrasound. Therefore, although the invention is described herein in the context of a CT imaging system, it should be understood that the invention is not limited to practice in CT and can be used in other modalities as well.

Figure 1:
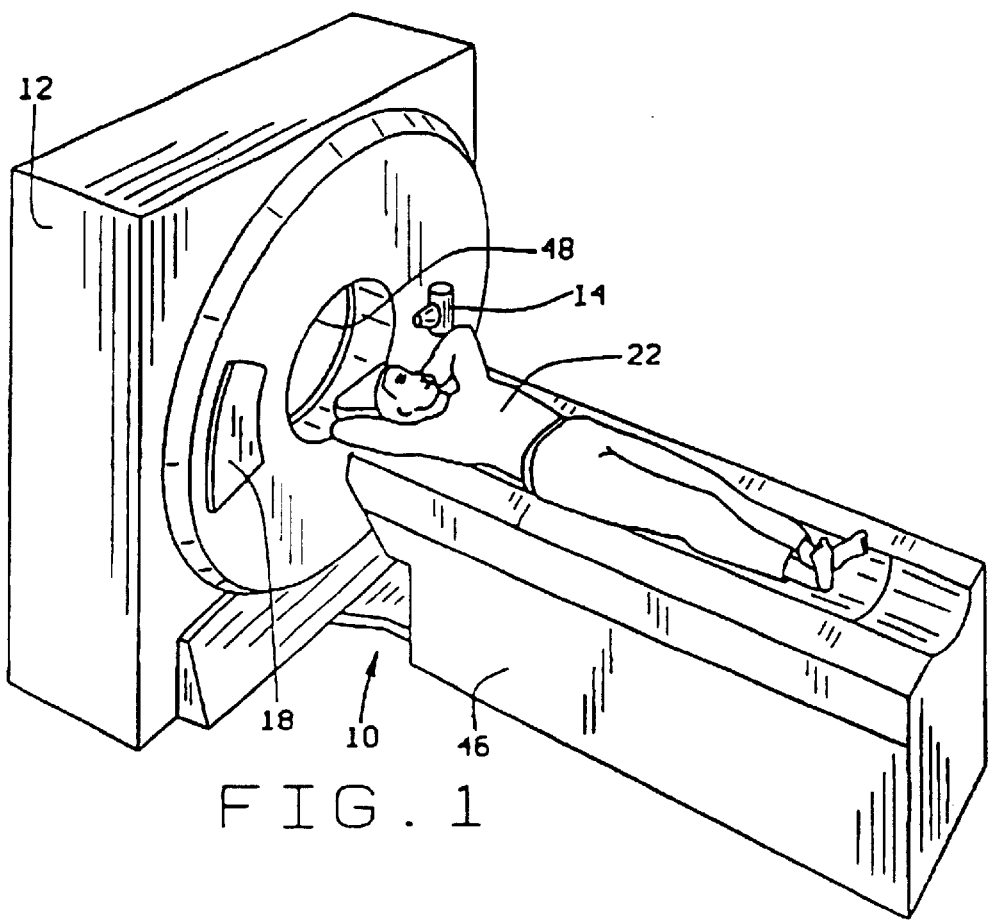
FIG. 1 is a pictorial view of a CT imaging system.
Figure 2:
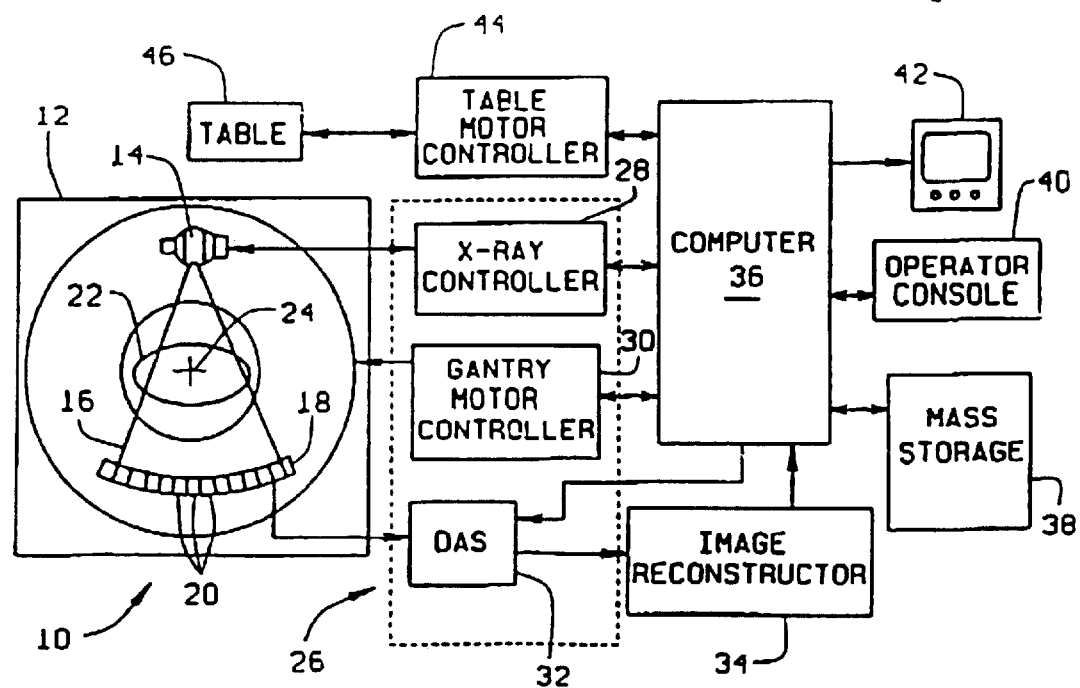
FIG. 2 is a block schematic diagram of the CT imaging system of FIG. 1.

With respect to CT, and referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through a medical patient 22. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

Figure 3:
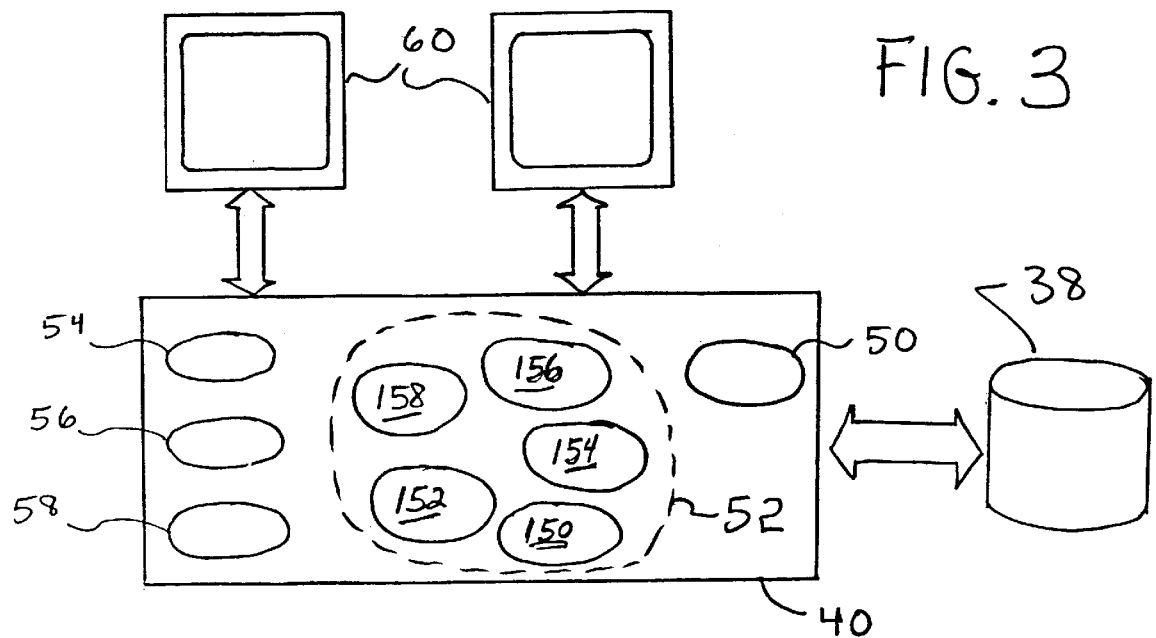
FIG. 3 is a block diagram of an operator console which forms part of the CT imaging system of FIG. 1.

FIG. 3 is a block diagram of operator console 40. In accordance with one embodiment, computer 36 (FIG. 1) is integrated into console 40, and console 40 includes an exam prescription subsystem 50 which specifies the manner in which the imaging system acquires data, a visualization subsystem 52 responsible for the presentation layout and display of the acquired images and processed data, an archive subsystem 54 for permanent storage and future retrieval of imaging data, a filming subsystem 56 which transfers data onto film, and a networking subsystem 58 that transfers data via a network to or from other imaging systems. Optional remote viewing stations may be coupled to console 40 to enable the remote viewing of images.

Exam prescription subsystem 50 is responsible for determining how the patient exam data is acquired. Numerous parameters are required to specify an acquisition including a sequence of slice locations, slice thickness, field-of-view, scanning technique, and reconstruction algorithm. Volume imaging and filming presentation parameters may also be included in the exam scan prescription. These parameters can be entered explicitly by the technologist or, more commonly, the parameters are defined by selecting a particular scan protocol as is well known in the art. Subsystem 50 generates a scan prescription and the prescription is transmitted to DAS 32 (FIG. 2).

Figure 4:
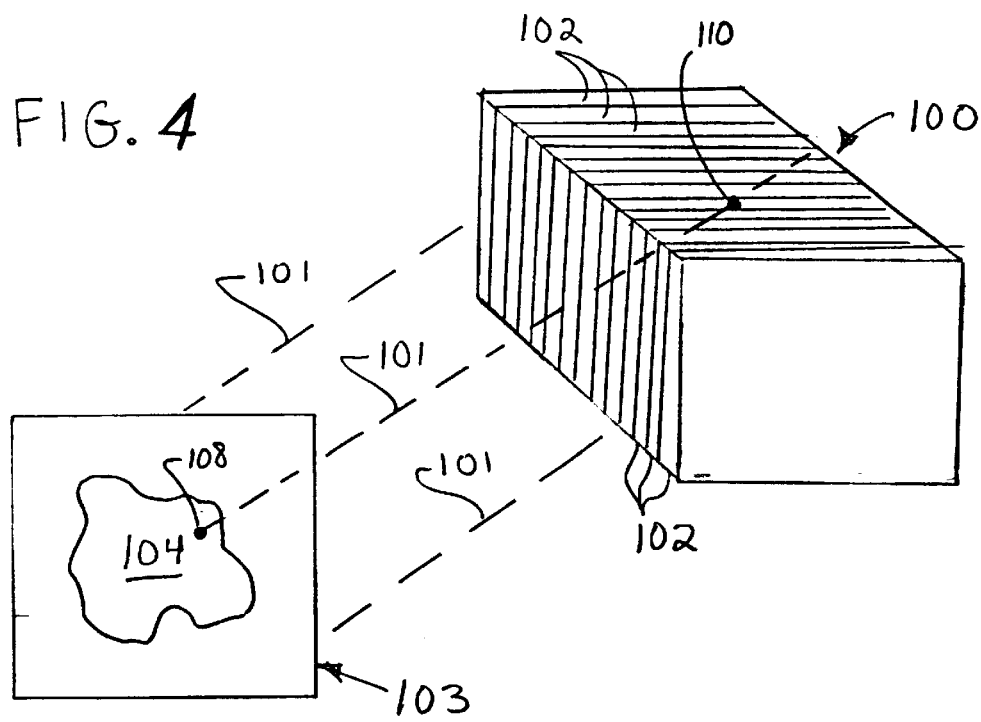
FIG. 4 is a schematic representation of a 3D image data set acquired with the CT imaging system of FIG. 1 and its projection onto a 2D plane.

DAS 32 collects the acquisition data in accordance with the prescription, and provides the acquired data to image reconstructor 34 for generating a series of imaged from the acquired data which can be used to produce a 3D image data set. A 3D image data set includes a three-dimensional (or higher) rectilinear array of values, often with a single scalar value per sample. FIG. 4 illustrates a 3D image data set 100 which is constructed from a stack of two-dimensional slice images 102. During acquisition, individual slices are acquired and stacked along one dimension of the 3D image data set. After all slices have been acquired and reconstructed a 3D image data set 100 containing $N_x$ by $N_y$ by $N_z$ data samples is produced.

Referring again to FIG. 3, visualization subsystem 52 controls presentation of all relevant imaging data to the operator. The data stored in memory 38 includes, for example, 2D images, 3D projections, patient data, annotation, and measurements. Subsystem 52 implements several visualization features such as routine display 150, cross reference 152, autoview display 154, volume autoview display 156, and other forms of display 158, using one or more windows or viewports 60. Visualization subsystem 52 also includes several components to filter, classify, render, annotate, and take measurements.

Visualization subsystem 52 supports the real-time display of 2D cross sectional data and the real-time display of 3D data. This visualization feature is referred to as "Autoview". "Volume Autoview", as used herein, refers to an incrementally updated 3D view of the data as the data is being acquired. Volume Autoview attaches to the imaging "stream" from the image reconstructor 34 and is executed at console 40.

During data acquisition, Volume Autoview provides a real-time, incrementally updated, 3D view of the data as the data is acquired over time. This method of rendering is referred to herein as dynamic data rendering (DDR). After the image data has been completely acquired, a method of rendering for static data may then be utilized. This method of display is referred to herein as static data rendering (SDR).

Prior to data acquisition, an exam is prescribed by the technologist. Volume Autoview is integrated with the exam prescription subsystem, providing parameters which specify how the dynamic volume(s) should be visualized during the data acquisition. More particularly, parameters such as position and orientation of the 3D model and view, color and transparency assignments, filter and segmentation settings, visualization technique and reconstruction algorithm are specified in the protocol. The visualization parameters are also contained in specific VIS scan protocols.

Referring to FIG. 4, as new 2D slice images 102 are acquired, visualization subsystem 52 filters the images (if necessary) as they are added to the 3D image data set 100. Two- and three-dimensional segmentation is also possible for extracting specific information from the images with the constraint that all processing and rendering must "keep pace" with the image generation rates of the data acquisition subsystem.

As illustrated in FIG. 4, the acquired 3D image data set 100 is projected along rays 101 onto a 2D image plane 103 for display as an index image 104 on a viewpoint 60. This is accomplished using well-known methods, for example, ray casting or texture mapping. The image projection technique known as ray casting (RC) casts a ray 101 from each pixel in the 2D image plane 103 into the 3D image data set 100. The 3D volume is then sampled along the ray and data values are combined to form a final pixel value for the index image 104. Samples may optionally be mapped to various quantities, such as color or opacity, to support common volume rendering techniques. Common operations applied to samples along the ray are maximum intensity (MIP), average, compositing, and compositing with shading.

Alternatively, a hardware texture mapping (TM) technique may be used to produce the index image 104 from the 3D image data set 100. Hardware TM is an object order technique wherein data samples are traversed and blended in the proper order using texture mapped geometric rendering hardware. The samples (or their RGBA mapped values) are mapped onto polygons and the polygons are projected onto the 2D image plane 103. Similar to RC, the data samples may be converted to other properties, such as color and opacity, to support common volume visualization rendering techniques. All operations on data samples available in RC are possible using a TM technique.

While the projected 3D index image 104 may provide sufficient information to make a diagnosis, many physicians prefer to see sectional images taken through the region of interest. Such sectional images are traditionally referred to as axial, sagital or coronal images, depending on their orientation with respect to the patient. The present invention enables the operator to identify a particular region of interest in the patient using the displayed 3D index image 104, and to prescribe the number and orientation of 2D sectional images for display. The projected 3D image 104 is thus used as an index into the massive 3D image data set 100 that may have been acquired.

Figure 6:
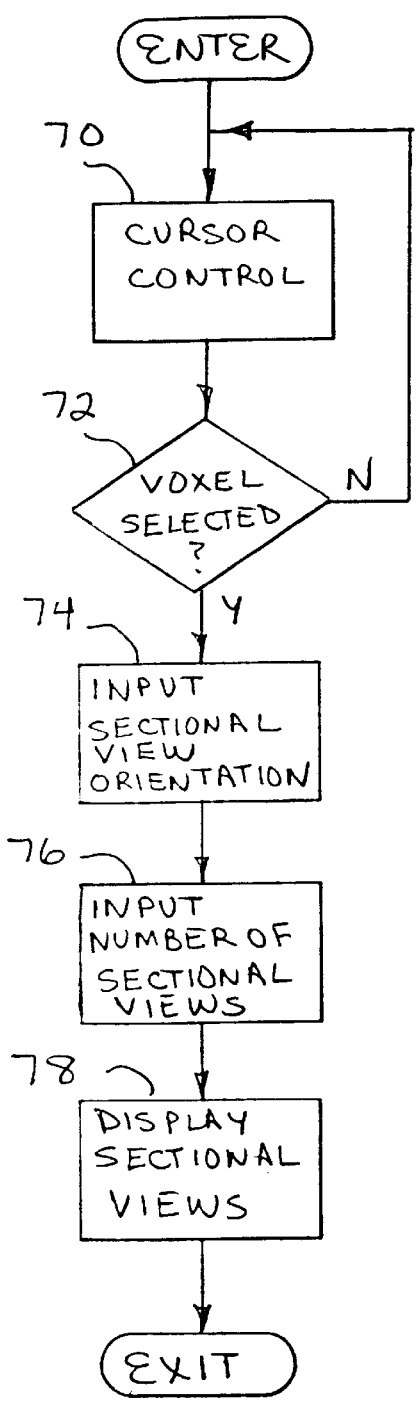
FIG. 6 is a flow chart illustrating the steps performed by the operator console of FIG. 3 to practice the preferred embodiment of the invention.
Figure 5:
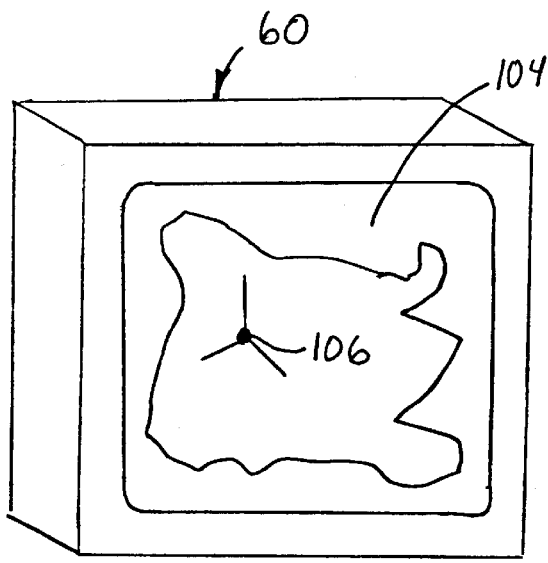
FIG. 5 is a pictorial representation of an exemplary index image produced by the CT imaging system of FIG. 1.

Referring particularly to FIGS. 5 and 6, the visualization subsystem 52 includes a cursor control 70 which is responsive to manual inputs from the operator console 40 to produce a cursor 106 on the index image 104. Using a track ball (not shown), the cursor 106 may be moved to any selected location. Such a cursor 106 is shown in the exemplary 3D projected image 104 of FIG. 5 as a 3-axis orthogonal cross-hair which directly selects a particular voxel in the 3D image data set 100. As shown in FIG. 4, an alternative choice is a cursor which designates a point 108 on the 3D projected index image 106. A ray 101 is cast from the image 104 back through the 3D image data set 100 at this selected point 108 and at the projection angle. The voxel lying 110 on this ray having the maximum intensity is selected.

After a particular voxel in the 3D image data set 100 has been selected as indicated at decision block 72, the operator is prompted to input the spatial orientation of the desired 2D sectional views as indicated at block 74. In the preferred embodiment either an axial, sagital or coronal view orientation may be selected, although it can be appreciated that oblique images might also be selected with the entry of appropriate angles.

As indicated at process block 76, the operator is then prompted to enter the number of sectional images to be displayed. These may include anywhere from 1 to 1000 slices and the resulting set of sectional images are centered on the previously selected voxel and oriented in the previously selected direction. The selected sectional images are displayed on the viewports 60 as indicated at process block 78 by extracting from the 3D image data set 100 the intensity data for each corresponding voxel.

The present invention enables the 3D image data set 100 which covers the entire prescribed field of view to be displayed as a projection on a 2D display device and used as an index. Using this index, the operator can easily select a particular region of interest in the 3D image data set 100 for further diagnosis. A set of 2D sectional images through this region of interest are selected and produced.

The massive amount of image data that may be acquired with a modern imaging system may thus be processed to enable the physician to quickly identify the particular region which requires detailed examination and to easily specify the type of 2D sectional diagnostic image that is desired of this region.

What is claimed is:

1. A method for displaying image data acquired with a medical imaging system, the steps comprising:
   a) reconstructing a 3D image data set with the acquired image data;
   b) producing an index image by projecting the 3D image data set;
   c) displaying the index image on a display device;
   d) producing a cursor on the display device which enables manual selection of a region of interest in the 3D image data set;
   e) receiving input data which indicates the number of 2D sectional images to be produced;
   f) receiving input data which indicates the spatial orientation of the 2D sectional images;
   g) producing the 2D sectional images by extracting corresponding image data from the region of interest in the 3D image data set; and
   h) displaying the 2D sectional images on a display device.

2. The method as recited in claim 1 in which the region of interest is selected by identifying a particular voxel in the 3D image data set.

3. The method as recited in claim 2 in which the particular voxel is identified by positioning the cursor.

4. The method as recited in claim 2 in which the particular voxel is identified by:
   projecting a ray into the 3D image data set from a location in the index image indicated by the cursor; and
   selecting a voxel in the 3D image data set which is intersected by the projection ray.

5. The method as recited in claim 4 in which the voxel is selected by determining the maximum intensity voxel intersected by the projection ray.

6. The method as recited in claim 1 in which step f) includes analyzing the input data to determine if the 2D sectional images are to be oriented in an axial, sagital or coronal direction.

7. The method as recited in claim 2 in which the particular voxel is at the center of the region of interest and the displayed 2D sectional images depict successive slices through the region of interest.

8. The method as recited in claim 1 in which the medical imaging system is a CT system which acquires a series of 2D slice images and step a) is performed by combining the series of 2D slice images to form the 3D image data set.

9. The method as recited in claim 8 in which steps a), b) and c) are performed as successive 2D slice images are being acquired by the CT system.

10. A CT system which comprises:
    means for acquiring a succession of 2D slice images from a prescribed field of view;
    means for combining the acquired 2D slice images to form a 3D image data set;
    means for producing an index image of the 3D image data set;
    means for using the index image for manually selecting a region of interest in the 3D image data set;
    means for manually indicating a number of 2D sectional images;
    means for manually indicating a spatial orientation of the 2D sectional images; and
    means for displaying indicated 2D sectional images by using data from corresponding voxels in the 3D image data set.

11. The CT system as recited in claim 10 in which the means for manually selecting a region of interest includes a display for presenting the index image and manually operable cursor means for identifying a location in the index image.

12. The CT system as recited in claim 11 in which the means for producing the index image includes means for projecting the 3D image data set along a projection axis onto a 2D image plane.

13. The CT system as recited in claim 12 in which the cursor means includes means for projecting a ray from the identified location in the index image into the 3D image data set and means for selecting a voxel therein which lies along the ray.

14. The CT system as recited in claim 13 in which the means for selecting a voxel selects the voxel having the maximum intensity.

15. The CT system as recited in claim 10 in which the means for manually indicating a spatial orientation is operable to indicate axial, sagital or coronal orientations.

16. The CT system as recited in claim 10 in which the means for producing an index image is operable while the succession of 2D slice images are being acquired by the first-named means.

* * * * *